US00PP20976P2

(12) United States Plant Patent
Konst

(10) Patent No.: US PP20,976 P2
(45) Date of Patent: May 4, 2010

(54) ***ALSTROEMERIA* PLANT NAMED 'KONAZUR'**

(50) Latin Name: *Alstroemeria hybrida*
Varietal Denomination: Konazur

(75) Inventor: Johannes Wilhelmus Maria Konst, Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 0 days.

(21) Appl. No.: 12/321,351

(22) Filed: Jan. 20, 2009

(51) Int. Cl.
*A01H 5/00* (2006.01)

(52) U.S. Cl. ..... Plt./309

(58) Field of Classification Search ..... Plt./309
See application file for complete search history.

*Primary Examiner*—Kent L Bell
(74) *Attorney, Agent, or Firm*—C. A. Whealy

(57) ABSTRACT

A new and distinct cultivar of *Alstroemeria* plant named 'Konazur', characterized by its compact and mounding plant habit; sturdy and strong plants; vigorous growth habit; light and dark red purple-colored flowers; and good garden performance.

2 Drawing Sheets

Botanical designation: *Alstroemeria hybrida.*
Cultivar denomination: 'KONAZUR'.

BACKGROUND OF THE INVENTION

The present invention relates to a new and distinct cultivar of *Alstroemeria* plant, botanically known as *Alstroemeria hybrida,* grown typically as a potted garden *Alstroemeria,* and hereinafter referred to by the name 'Konazur'.

The new *Alstroemeria* plant is a product of a planned breeding program conducted by the Inventor in Nieuwveen, The Netherlands. The objective of the breeding program is to create new compact potted garden *Alstroemeria* cultivars that flower early freely and have attractive foliage and flower coloration.

The new *Alstroemeria* plant originated from a cross-pollination made by the Inventor in Nieuwveen, The Netherlands on Jun. 30, 2003 of a proprietary *Alstroemeria hybrida* selection identified as code number 11248-15, not patented, as the female, or seed, parent with a proprietary *Alstroemeria hybrida* selection identified as code number 16336-4, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands on Jun. 13, 2005.

Asexual reproduction of the new *Alstroemeria* plant by root divisions in a controlled greenhouse environment in Nieuwveen, The Netherlands since Jun. 20, 2005, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Konazur'. These characteristics in combination distinguish 'Konazur' as a new and distinct cultivar of *Alstroemeria:*

1. Compact and mounding plant habit.
2. Sturdy and strong plants.

3. Vigorous growth habit.
4. Light and dark red purple-colored flowers.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are taller than plants of the female parent selection.
2. Plants of the new *Alstroemeria* have larger flowers than plants of the female parent selection.

Plants of the new *Alstroemeria* can be compared to plants of the male parent selection. Plants of the new *Alstroemeria* differ from plants of the male parent selection in the following characteristics:

1. Plants of the new *Alstroemeria* have thinner stems than plants of the male parent selection.
2. Plants of the new *Alstroemeria* have smaller flowers than plants of the male parent selection.

Plants of the new *Alstroemeria* can be compared to plants of the *Alstroemeria hybrida* 'Konpride', disclosed in U.S. Plant Pat. No. 20,050. In side-by-side comparisons conducted in Nieuwveen, The Netherlands, plants of the new *Alstroemeria* differed from plants of 'Konpride' in the following characteristics:

1. Plants of the new *Alstroemeria* were broader than plants of 'Konpride'.
2. Plants of the new *Alstroemeria* had longer leaves than plants of 'Konpride'.
3. Plants of the new *Alstroemeria* had larger inflorescences and larger flowers than plants of 'Konpride'.
4. Plants of the new *Alstroemeria* and 'Konpride' differed in flower color as plants of 'Konpride' had bright pink-colored flowers.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Konazur' grown in a container.

The photograph on the second sheet is a close-up view of typical flowers of 'Konazur'.

DETAILED BOTANICAL DESCRIPTION

The aforementioned photographs and following observations and measurements describe plants of the new *Alstroemeria* grown in Nieuwveen, The Netherlands during the spring and summer in 33-cm containers in a glass-covered greenhouse. During the production of the plants, day temperatures ranged from 6° C. to 30° C. and night temperatures ranged from 6° C. to 16° C. Plants had been growing for 36 weeks when the photographs and description were taken. In the following description, color references are made to The Royal Horticultural Society Colour Chart, 2001 Edition, except where general terms of ordinary dictionary significance are used.

Botanical classification: *Alstroemeria hybrida* 'Konazur'.

Parentage:

*Female, or seed, parent.*—Proprietary *Alstroemeria hybrida* selection identified as code number 11248-15, not patented.

*Male or pollen parent.*—Proprietary *Alstroemeria hybrida* selection identified as code number 16336-4, not patented.

Propagation:

*Type.*—By root divisions.

*Root description.*—Thick, fleshy; color, close to 161C.

*Rooting habit.*—Freely branching; dense.

*Rhizome description.*—Shape: Elongate; rounded. Length: About 5 cm. Diameter: About 8 mm. Texture: Smooth. Color: Close to 161C.

Plant description:

*Plant habit.*—Compact and mounded; freely branching, bushy appearance. Sturdy and strong plants; vigorous growth habit.

*Plant height.*—About 35 cm.

*Plant diameter* (*area of spread*).—About 50 cm.

Stem description:

*Aspect.*—Upright to outwardly spreading.

*Internode length.*—About 0.8 cm to 5.9 cm.

*Strength.*—Strong, sturdy.

*Texture.*—Smooth, glabrous.

*Color.*—Close to 146B.

Foliage description:

*Arrangement.*—Alternate; below the peduncles in a single whorl; all leaves sessile.

*Length.*—About 12.8 cm.

*Width.*—About 2.8 cm.

*Shape.*—Lanceolate.

*Apex.*—Acute.

*Base.*—Attenuate.

*Margin.*—Entire.

*Texture, upper surface.*—Smooth, glabrous.

*Texture, lower surface.*—Pubescent.

*Venation pattern.*—Parallel.

*Color.*—Developing leaves, upper and lower surfaces: Close to 137C. Fully expanded leaves, upper surface: Close to 137B; venation, close to N144A. Fully expanded leaves, lower surface: Close to 137C; venation, close to 144A.

Flower description:

*Flower type and habit.*—Single cup-shaped flowers arranged in compound umbels; flowers face mostly outwardly; freely flowering habit; about four to twelve flowers per inflorescence; about 40 to 75 flowers develop per plant.

*Natural flowering season.*—Flowering continuous from the late spring until the autumn in The Netherlands.

*Fragrance.*—None detected.

*Flower longevity on the plant.*—About one to three weeks; flowers not persistent.

*Flower longevity as a cut flower.*—About one to two weeks; flowers not persistent.

*Flower buds.*—Length: About 4.7 cm. Diameter: About 1.3 cm. Shape: Ovoid. Color: Close to 53A, venation, close to 143A; towards the apex, close to 70A.

*Umbel height.*—About 12.5 cm.

*Umbel diameter.*—About 18 cm.

*Flower diameter.*—About 6.1 cm.

*Flower depth* (*height*).—About 6.8 cm.

*Perianth.*—Arrangement: Six arranged in two whorls, each whorl with two lateral and one median segments. Size, inner perianth: Length, lateral segments: About 5.9 cm. Width, lateral segments: About 1.5 cm. Length, median segment: About 5.3 cm. Width, median segment: About 1.5 cm. Size, outer perianth: Length, lateral segments: About 5.2 cm. Width, lateral segments: About 2.5 cm. Length, median segment: About 5.6 cm. Width, median segment: About 2.4 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Embedded point. Base, inner and outer perianths, lateral and median segments: Attenuate. Margin, inner perianth, lateral and median segments: Entire. Margin, outer perianth, lateral and median segments: Crenate. Texture, inner and outer perianths, lateral and median segments: Smooth, glabrous. Color, inner perianth: When opening, lateral segments, upper surface: Towards the base, close to 75B; towards the apex, close to 72B; mid-section, close to 1B; stripes, close to 72A. When opening, median segment, upper surface: Close to 72B; stripes, close to 72A. When opening, lateral segments, lower surface: Towards the base, close to 75A; towards the apex, close to 72A; mid-section, close to 1B. When opening, median segment, lower surface: Close to 72B. Fully opened, lateral segments, upper surface: Towards the base, close to 75B; towards the apex, close to 72B; center, close to 13B; stripes, close to 72A. Color becoming closer to N78C with development. Fully opened, median segment, upper surface: Close to 70B; stripes, close to 72A. Color becoming closer to N78C with development. Fully opened, lateral segments, lower surface: Towards the base, close to 75A; towards the apex, close to 77B; apical spot, close to 72A; center, close to 1B. Fully opened, median segment, lower surface: Close to 77B; stripes, close to 72A. Color, outer perianth: When opening, lateral segments, upper surface: Close to 72B; central spot, close to 70A. When opening, median segments, lower surface: Close to 72B; central spot, close to 70A; towards the base, close to 77C. When opening, lateral and median segments, lower surface: Close to 77B; central spot, close to 71A; venation, close to 141A. Fully opened, lateral and median segments, upper surface: Close to 72B; central spot, close to 70A. With development, color becoming closer to 77B; central spot, close to 71A. Fully opened, lateral and median segments, lower surface: Close to 72B; central spot, close to 70A; venation, close to 141A.

*Pedicels.*—Length: About 1.5 cm. Diameter: About 3 mm. Strength: Strong. Angle: About 15° to 45° from vertical. Texture: Smooth, glabrous. Color: Close to 137B to 137C.

*Reproductive organs.*—Stamens: Quantity per flower: Six. Anther shape: Oval. Anther size: About 8 mm by 2 mm. Anther color: Close to N199A. Pollen amount: Abundant. Pollen color: Close to N186A. Pistils: Quantity per flower: One. Pistil length: About 5.5 cm. Style length: About 4.3 cm. Style color: Close to 64B; towards the base, close to 75C. Stigma color: Close to 64B. Ovary color: Close to 146B.

*Fruits.*—Length: About 1.5 cm. Diameter: About 1 cm. Color: Close to 200C.

*Seeds.*—Quantity per fruit: About three to ten. Length: About 5 mm. Diameter: About 5 mm. Color: Close to 165A.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures ranging from about 6° C. to about 30° C.

It is claimed:

1. A new and distinct *Alstroemeria* plant named 'Konazur' as illustrated and described.

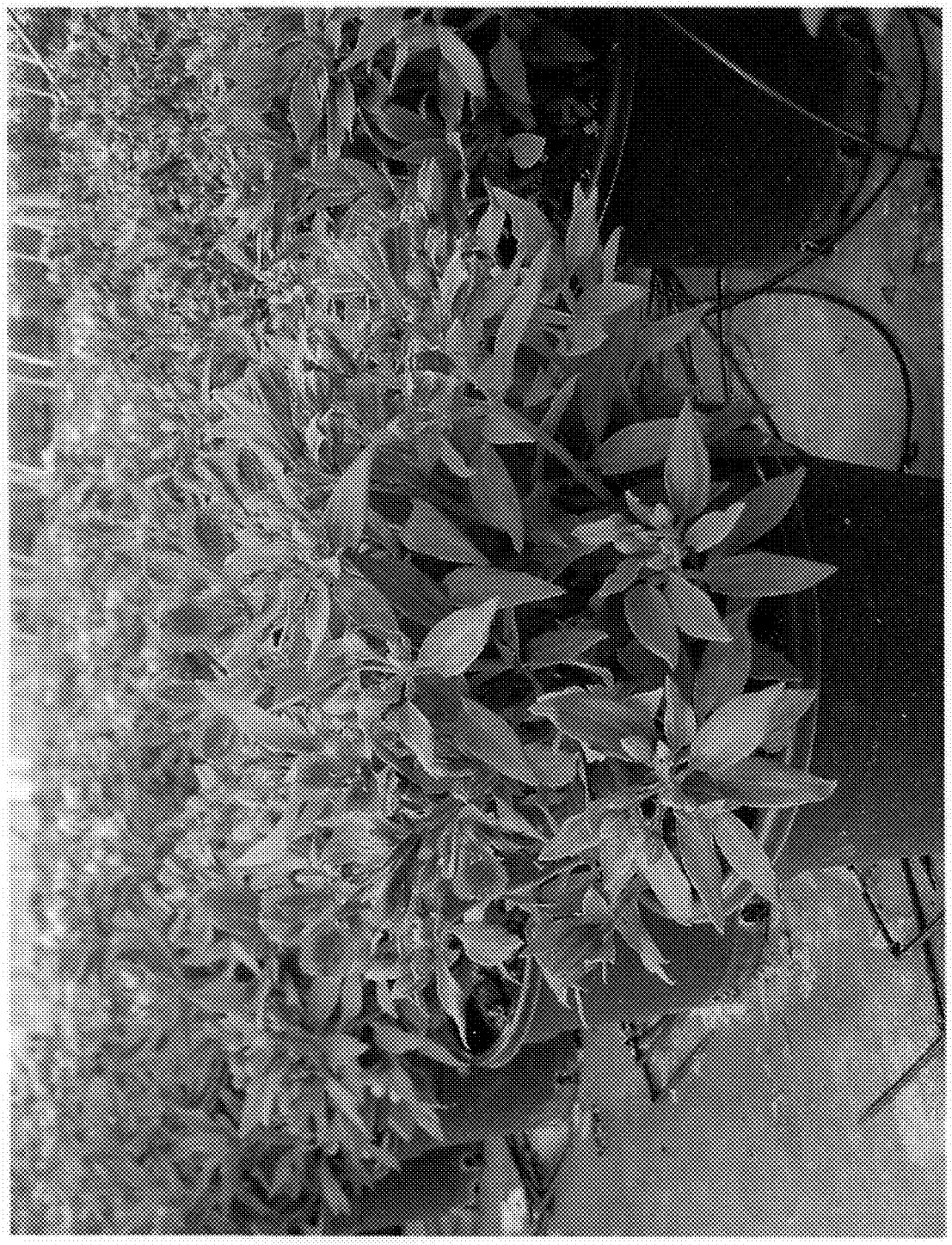

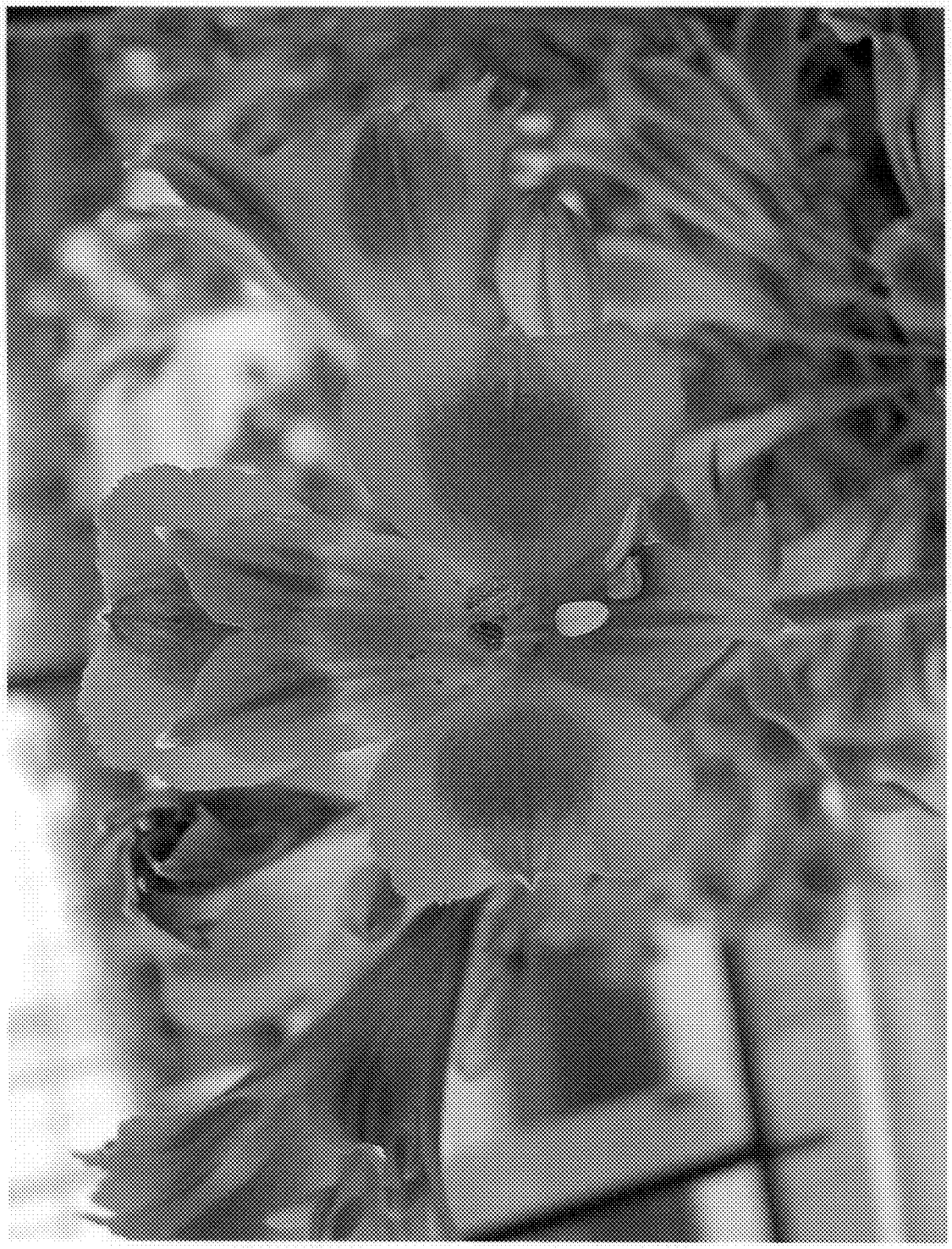

* * * * *